United States Patent [19]

Kessler

[11] 4,324,067
[45] Apr. 13, 1982

[54] ALGAL CELL HARVESTING

[75] Inventor: John O. Kessler, Tucson, Ariz.

[73] Assignee: The University of Arizona Foundation, Tucson, Ariz.

[21] Appl. No.: 118,585

[22] Filed: Feb. 4, 1980

[51] Int. Cl.³ .............................................. A01G 7/00
[52] U.S. Cl. ........................................................ 47/1.4
[58] Field of Search .................................... 47/1.4, 59

[56] References Cited

U.S. PATENT DOCUMENTS

| | | | |
|---|---|---|---|
| 3,468,057 | 9/1969 | Buisson et al. | 47/1.4 X |
| 3,577,678 | 5/1971 | Burton | 47/1.4 X |
| 3,598,726 | 8/1971 | Welch | 47/1.4 X |
| 3,780,471 | 12/1973 | Ort | 47/1.4 |
| 4,055,491 | 10/1977 | Porath-Furedi | 47/1.4 X |
| 4,115,949 | 9/1978 | Avron et al. | 47/1.4 |
| 4,199,895 | 4/1980 | Avron et al. | 47/1.4 |

FOREIGN PATENT DOCUMENTS 2102926  4/1972  France .................................. 47/1.4

OTHER PUBLICATIONS

Agal cultures . . . , Fogg, Univ. Wisconsin Press, 2nd ed., circa Mar. 1976.
Science, vol. 206, Nov. 30, 1979, p. 1053.
Solar bioconversion . . . , Williams et al., in Biotechnology In Energy Production & Conservation, J. Wiley & Sons, N.Y., 1979, pp. 115-130.

Primary Examiner—Robert E. Bagwill
Attorney, Agent, or Firm—Mason, Kolehmainen, Rathburn & Wyss

[57] ABSTRACT

The present invention relates to systems, processes and apparatus for harvesting microorganisms, especially free swimming unicellular algae, such as algal cells of the Dunaliella variety.

In accordance with one aspect of the invention, a material mass made up of fibrous or inert inorganic material in interposed between the liquid containing reservoir in which the algal cells are disposed for multiplication by cell division and the cell harvest zone to provide a preferred travel path for the migration of the cells from the reservoir to the harvest zone. This mass not only enhances cell travel from the reservoir to the harvest zone, but also acts as a cell collision mass to enhance cell division, thereby to decrease the time lag of cell division build-up in the early stages of generating an algal cell culture in the reservoir. Means are also provided for transferring the concentrated algal cell culture from the harvest zone to a collection zone and for recycling at least a portion of the concentrated culture back to the growth reservoir.

26 Claims, 11 Drawing Figures

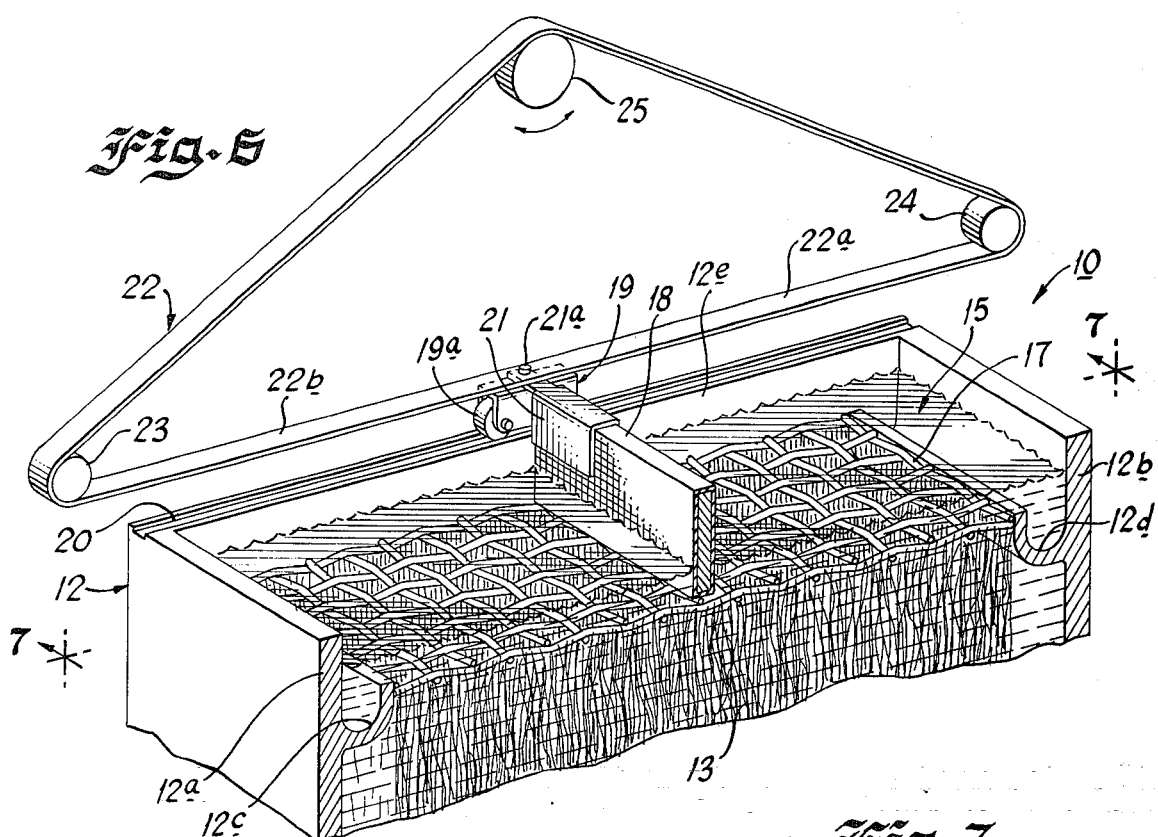
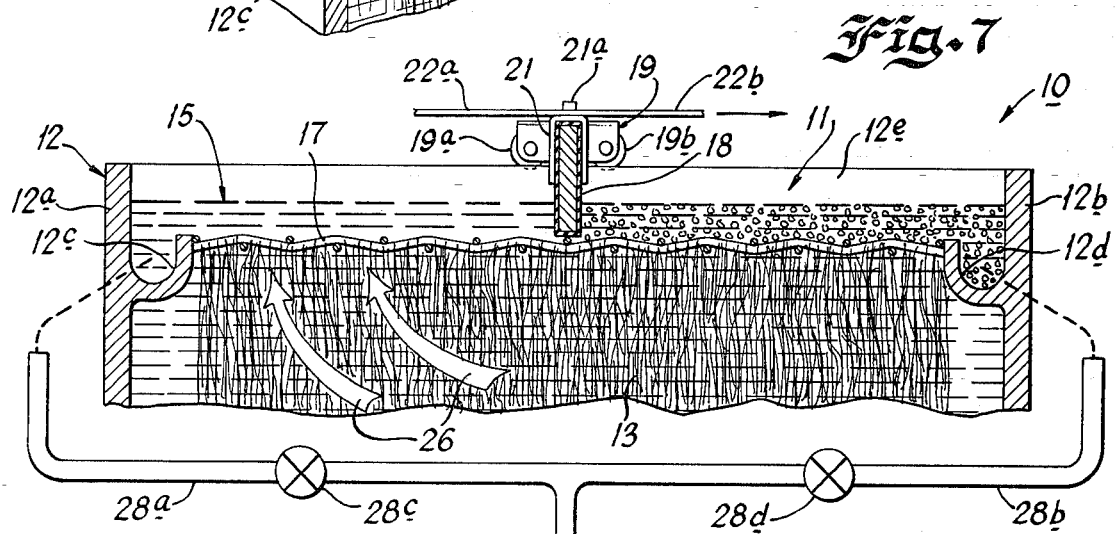
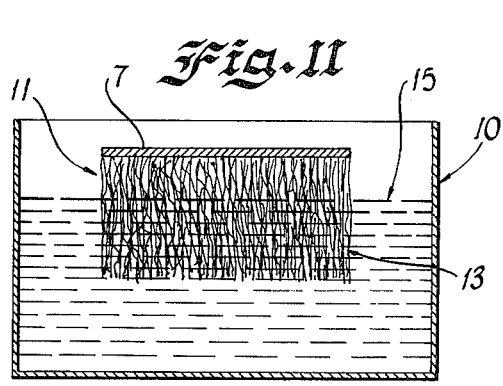

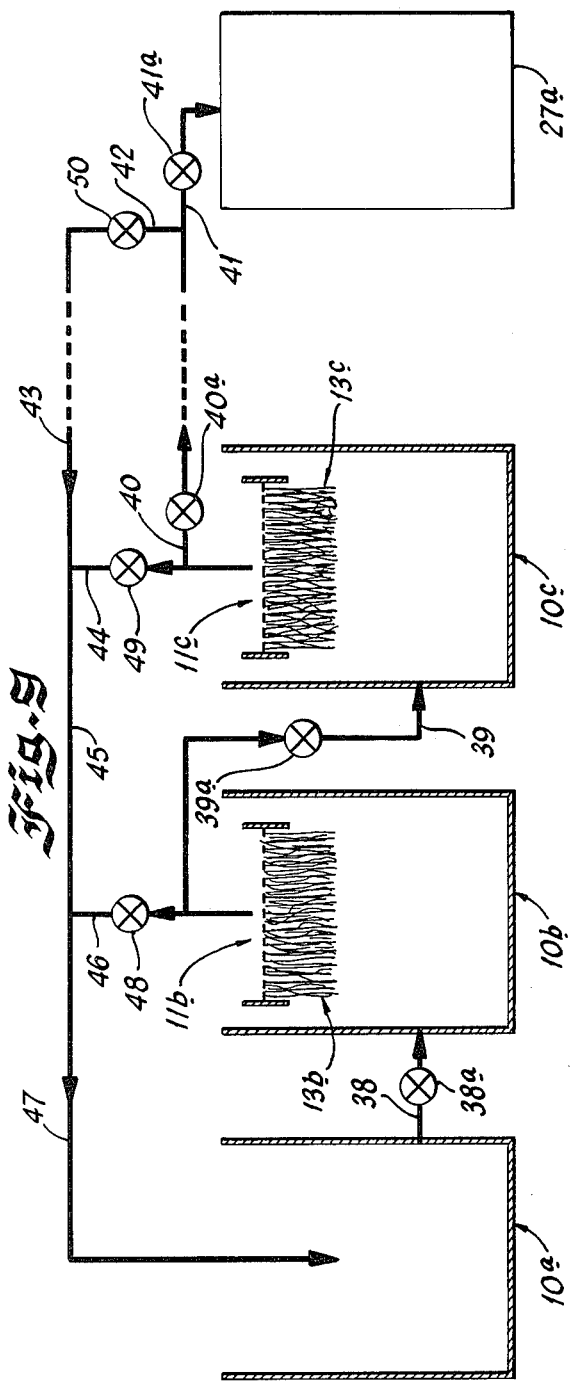

4,324,067

ALGAL CELL HARVESTING

The present invention relates to systems, processes, and apparatus for harvesting motile swimming microorganisms, especially unicellular algae, and more particularly to the harvesting of algal cells of the Dunaliella variety.

The useful products yielded by the growth and harvesting of the alga Dunaliella are well explained in a paper published by L. A. Williams, E. L. Foo, A. S. Foo, I. Kuhn, and C. G. Heden in 1978 in the article appearing in the book BIOTECHNOLOGY IN ENERGY PRODUCTION AND CONSERVATION published by John Wiley & Sons, New York, 1979, entitled "Solar Bioconversion Systems Based on Algal Glycerol Production". In this book at pages 115 to 130, inclusive, the authors point out that harvested and suitably processed Dunaliella cells can be an important source of glycerol, $\beta$-carotein, human and animal nutriments and other useful cellular product chemicals. Dunaliella and other algal cells subject to the culture and harvest techniques herein described may also be considered, together with their cellular products, as a fuel or a fuel precursor, resulting from the conversion of solar energy into biomass by said algae. It is also well known that Dunaliella cells self-multiply by cell division as a function of time when disposed in saline water, such as brackish water or sea water, or more concentrated saline solutions, and are fed adequate nutriments including, as major components, carbon dioxide and light, usually sunlight. In such an environment, the cells are free swimming and multiply by well known and naturally occurring cell division processes. It is believed that among other factors, the rate of cell multiplication is dependent upon or a function of the collision rate of the free swimming cells with each other and with other bodies. One process for stimulating and enhancing the division and hence the cell multiplication rate of the Dunaliella cells is described in U.S. Pat. No. 4,115,449 issued to Avron and Ben-Amotz, both of Israel, on Sept. 26, 1978. In spite of the extensive scientific effort which has been expended in studying the behavior of Dunaliella cells and in attempts to enhance the cell density of Dunaliella cell populated reservoirs, and as pointed out in the above referenced book at pages 51 to 68 inclusive no economically adequate techniques have heretofore been developed for harvesting the cells.

Accordingly, it is an object of the present invention to provide improved systems, processes and apparatus for harvesting free swimming motile algal cells.

It is another object of the invention to provide improved systems, processes, and apparatus of the character described which are particularly useful in harvesting algal cells of the Dunaliella genus.

It is a further object of the invention to provide improved cell harvesting systems, processes, and apparatus of the character indicated which require a minimal amount of externally supplied energy in the performance of the harvesting operation.

A still further object of the invention is to provide a harvesting system of the character described wherein enhancement of the cell division rate is achieved incident to the cell harvesting operation.

Still another object of the invention is to provide a cell harvesting system of the character described which functions without dilution or contamination of the cell growth medium.

It is a still further object of the invention to provide a harvesting system of the indicated character in which microorganisms are employed to facilitate the cell harvesting operation.

It is still another object of the invention to provide cell harvesting systems and apparatus of the character indicated which are non-destructive and non-damaging as far as the cells are concerned, thus allowing for the feedback or recycling of a portion of the harvested cells into the fluid medium used for supporting the algal growth and cell division, whereby selective genetic improvement of the algal cell strain is achieved, especially in terms of the speed and efficiency with which the cells swim into and traverse the harvesting system.

It is a still further object of the invention to provide cell harvesting apparatus of the described character which yields a highly concentrated algal cell suspension that can be guided into vessels where the cells can be sedimented by standard chemical methods, such as flocculation, without contaminating the main body of the cell growth medium, or by the method of maintaining the cell suspension in the dark, thereby inducing the cells to sediment and thus allow for simple bottom-withdrawal of the concentrated cell agglomerate.

It is another object of the invention to provide improved apparatus and an improved method for increasing the glycerol yield of algal cells of the Dunaliella genus by inducing naturally occurring migration of the cells from a saline liquid growth medium to a concentrated harvest zone and very substantially increasing the salinity of the residue liquid growth medium present in the harvest zone through evaporation of the residue liquid growth medium, either by exposure of the residue liquid growth medium to the environment in which the residue liquid growth medium is disposed or artificially, thereby to increase the glycerol content of the algal cells.

The invention, both as to its organization and certain preferred modes of practicing the same, together with further objects and advantages thereof, will best be understood by reference to the following specification, taken in connection with the accompanying drawings, in which:

FIG. 6 is a sectionalized perspective view illustrating in more detail one mechanism for removing the algal cells from the harvest zone forming a part of the system shown in FIG. 1;

FIG. 7 is a partial sectional view, taken along the lines 7—7 in FIG. 6 diagrammatically illustrating the manner in which the harvested algal cells may be transferred from the harvest zone shown in FIG. 6 to a collection chamber or reservoir;

FIG. 8 is a view, partially in section, diagrammatically illustrating one method of modifying the system shown in FIGS. 6 and 7 to recycle a portion of the harvested algal cells back into the liquid growth medium;

FIG. 9 schematically illustrates another system arrangement for recycling a portion of the harvested algal cells back into the liquid growth medium;

FIG. 10 schematically illustrates a modified system arrangement for harvesting the algal cells; and FIG. 11 illustrates a modification of the system shown in FIG. 10.

Figure 1:
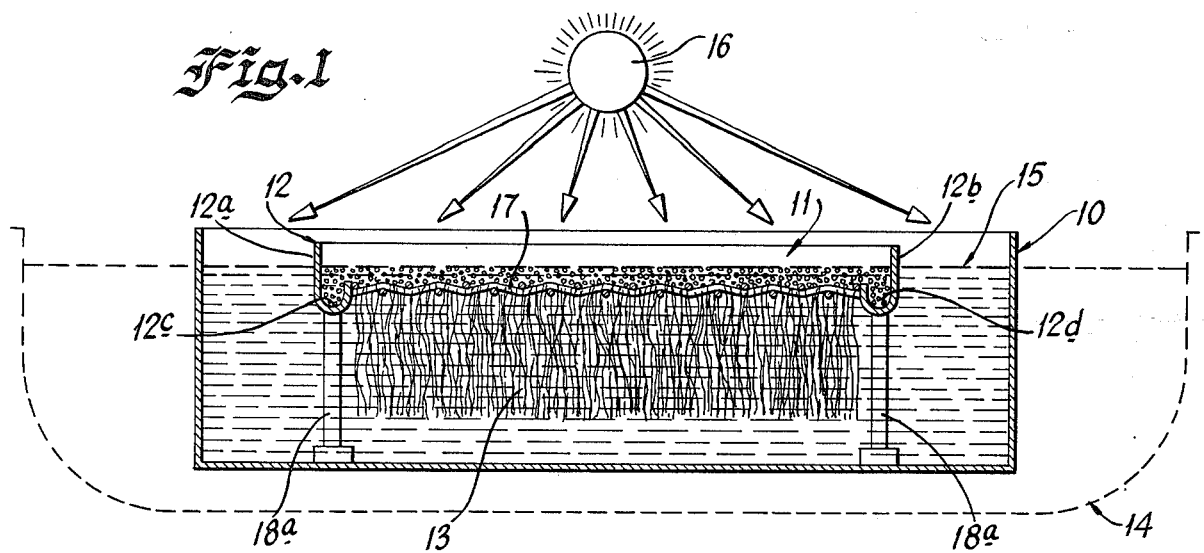
FIG. 1 is a view, partially in section, diagrammatically illustrating one mode of practicing the invention.
Figure 2:
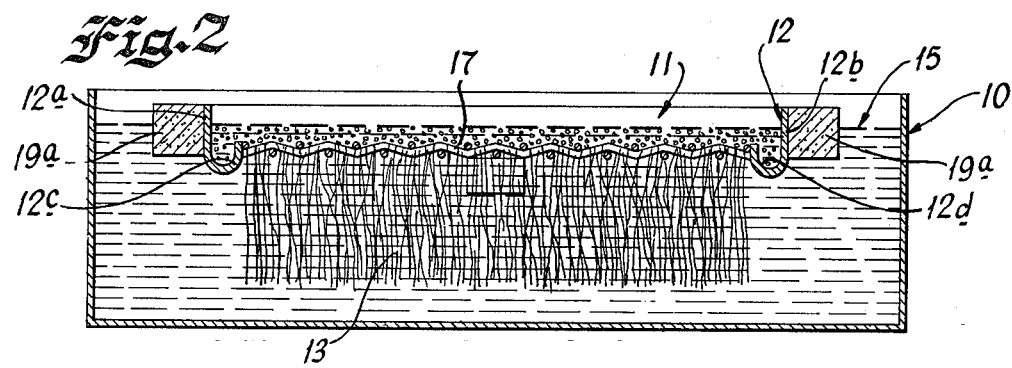
FIG. 2 illustrates a modification of the system shown in FIG. 1.

Referring now to the drawings and more particularly to FIG. 1 thereof, the improved Dunaliella cell growth and harvesting system there shown generally comprises a cell growing reservoir 10, a cell harvesting zone 11 in the form of a trough 12, and means in the form of a material mass 13 at least partially submerged in the liquid which fills the reservoir 10 for providing a preferred travel path for cells migrating from the liquid in the reservoir 10 to the harvest zone 11. As shown in FIG. 1, the reservoir 10 is in the form of a liquid containing tank although as indicated by the dashed line outline 14 in this figure, the reservoir 10 may be in the form of a lake or pond, artificial or naturally occurring.

As will be understood, the reservoir 10 is filled to the illustrated level with water indicated at 15, such as seawater, treated fresh water, or brackish water, of the appropriate salinity, i.e. NaCl concentration and containing other appropriate chemicals, such as nitrogen compounds, and other organic and inorganic nutriments and minerals thereby supplying the necessary nutriments to the Dunaliella and/or other cells disposed within the body of water filling the reservoir. Also, the water 15 is exposed to the environmental air and is exposed to sunlight indicated at 16, or to an alternate source of artificial light. Thus division of the Dunaliella or other cells and enhanced cell concentration in the water contained in the reservoir 10 is effected in a manner well understood in the art.

The trough 12 consists of side members 12a and 12b shaped to define internally disposed channels 12c and 12d and suitably interconnected at their ends by end members, not shown, thereby to form a generally rectangular frame. An open mesh screen or perforated plate 17 extends between and is connected to the side and end members to provide support for the submerged material mass 13 and to permit migration of the algal cells to the harvest zone 11. In the embodiment of the invention illustrated in FIG. 1 of the drawings, the material mass 13 comprises elongated fibers which are looped or otherwise secured to the elemental parts of the screen or perforated plate 17 and extend downwardly from the bottom of the screen or plate 17 into the liquid medium within the reservoir 10. These fibers are loosely disposed in the liquid medium within the reservoir and may be of any suitable organic or inorganic material which is not toxic to the algal cells with which they come in contact. For example, cotton or other plant fibers may be used. Alternatively, plastic fibers, glass wool or rock wool, or certain varieties of stainless steel fibers or composite fibers may be employed. In addition, woven or felted materials may be used to form the mass 13. As will be understood, the fibrous material mass 13 may extend from the screen or plate 17 partially toward the bottom of the reservoir 10 or may extend all the way to the bottom of the reservoir to form a material mass column which terminates at its upper end in the harvest zone 11. For the purpose of supporting the cell harvesting assembly within the reservoir 10, upright posts 18a are provided which rest upon the bottom of the reservoir and are connected at their top ends to the side members 12. As will be understood, these posts are located at spaced intervals longitudinally of the side members 12 to provide the necessary overall support for the cell harvesting assembly.

As will be understood, the support of the depicted harvesting system may also be entirely or partially accomplished by floating support members 19a, attached to the side members 12, and, as may be required, to the screen or plate 17. Intermittent retraction or elimination of the posts 18a then permits repositioning of the harvest system within the reservoir 10, or within the larger reservoir volume 14.

The harvest of cells from the reservoir 10 into the harvest zone 11 by means of the system described depletes the store of cells which are available for future harvest in the vicinity of the material mass 13. It will be understood that motions of the material mass 13 and the cell containing liquid within the reservoir 10 relative to one another serve to supply and present undepleted cell containing liquid to the material mass 13. Such relative motions can be arranged by moving or floating a harvest system comprised of parts of the kind illustrated in FIG. 1 through the reservoir 10, or by arranging for a slow flow of the liquid within the reservoir 10 through and past the harvest system, and in particular through and under the material mass 13, or by a combination of such motions, where paddles, propellers, tidally driven flows, evaporation depletion, chains, cables, ropes or other well known arrangements may be utilized to achieve the required relative motions.

It will furthermore be understood that whereas the sole use of the floats 19a specifies the depth of the harvest zone 11, independent of the liquid level 15, and the sole use of the posts 18a, or other rigid supports, specifies the absolute elevation of the harvest zone, optimal management of the growth reservoirs and associated harvest system may require either or both support members 18a and 19a at various times in the growth and harvest cycle.

Referring now more particularly to the manner in which the algal cells are grown and harvested in the system shown in FIG. 1 and described above, it will be understood that to initiate the cell growth process, the liquid medium in the reservoir 10 is stocked with unicellular algal cells of the selected variety, such as cells of one of the species of the Dunaliella genus. These cells have the characteristic of multiplying rapidly by cell division when disposed in an appropriate liquid growth medium of the above described character which is exposed to light, such as sunlight, and air, such as environmental air.

Cell division and hence cell multiplication is a natural process of the individual cells (sexual reproduction which requires interaction of two cells not being discussed in the present context). The time interval between cell division depends upon species-specific endogenous factors, as well as various environmental factors which include illumination, temperature, and the availability and assimilation of nutriments. The collision of cells with each other and with other bodies can enhance and increase the availability to the colliding cell of such nutriments and by this or other means result in a reduction of the time interval between cell divisions, i.e. an increase in the cell division rate. Moreover, it is believed and laboratory tests clearly indicate that the cell division and hence the cell multiplication rate is very substantially increased as a result of introducing fibrous material into the cell sustaining liquid, under conditions when the overall average cell concentration is low, as in lag phase.

Laboratory tests have clearly established that provision of the above described material mass 13 in the liquid growth medium in the manner illustrated in FIG. 1 of the drawings provided a preferred travel path for migration of the algal cells from the growth medium in the reservoir 10 to the harvest zone 11. Thus, typical algal cell concentrations in high growth culture media which are capable of sustaining high cell growth rates are less than $10^7$ cells per cubic centimeter of growth media and usually more like $10^6$ cells per cubic centimeter. For certain species of Dunaliella cells, for example, the typical ratio of liquid growth medium volume to cell volume is approximately 10,000 to 1. Thus, conventionally, 10 liters of solution must be processed to obtain 1 ml of algal cells or somewhat less than this volume of cell extracts.

As contrasted with the above given cell concentrations in the liquid growth medium, it has been found that by utilizing harvesting systems of the form illustrated in FIG. 1 and described above, the cell concentrations achieved in the harvest zone 11 over a period of 24 hours typically exceed the cell concentration in the liquid growth medium within the reservoir 10 by a factor of at least ten to one.

The concentration increase achieved by the method, and the time required to achieve that increase, depend on the specific geometries of the reservoir 10, of the harvest zone 11, of the material mass 13, and, additionally, on the generally prevalent levels of concentration of algal cells, as well as on their average swimming velocity under the prevailing conditions. Cell concentrations achieved in the harvest zone over a period of 24 hours have been observed to exceed the cell concentrations in the liquid growth medium 15 contained in the reservoir 10 by a factor of more than 100 to one. It will furthermore be understood that when the harvest zone geometry depicted in FIG. 3 is utilized, even very much greater concentration ratios are easily achieved.

The exact phenomenon which causes the relatively rapid migration of the algal cells from the liquid growth medium in the reservoir 10 through the material mass 13 to the harvest zone 11 is not understood. It is believed that one factor which may result in the said migration derives from the fleeting collisional interaction of the algal cells with each other and with the material of the material mass 13, and from a difference between the collision probabilities of upswimming and downswimming cells. It is also believed that a second factor which may be important in the genesis of the said phenomenon is the viscous damping of liquid flows by the material of the material mass 13. It is known that illumination 16 from the top and through the harvest zone, in the case of the system described herein, can enhance the ascent rate of the algal cells through the material mass 13, but it is also known from laboratory tests utilizing and contrasting the effect of directionally incident and uniformly applied illumination that the effect of such directional illumination is incidental and not a crucial part of the ascent phenomenon, or of the associated harvest scheme described herein.

It is also known that the free swimming algal cell bodies characteristically have flagella which they use to effect rapid swimming movement through the liquid growth medium. It is believed, moreover, that division of the algal cells is materially increased within the material mass 13 due to the collision of the cell bodies with the elemental components of this mass and with each other within this mass. Whatever the cause, it has been established that the described increased cell concentration in the harvest zone 11 does in fact occur when the above described cell harvesting system is employed. It will be noted, moreover, that the described cell concentration within the harvest zone is achieved without destruction of or harm to the algal cells and without the use of externally supplied energy, i.e. heat, electrical or mechanical energy, to produce the desired cell concentration.

Figure 3:
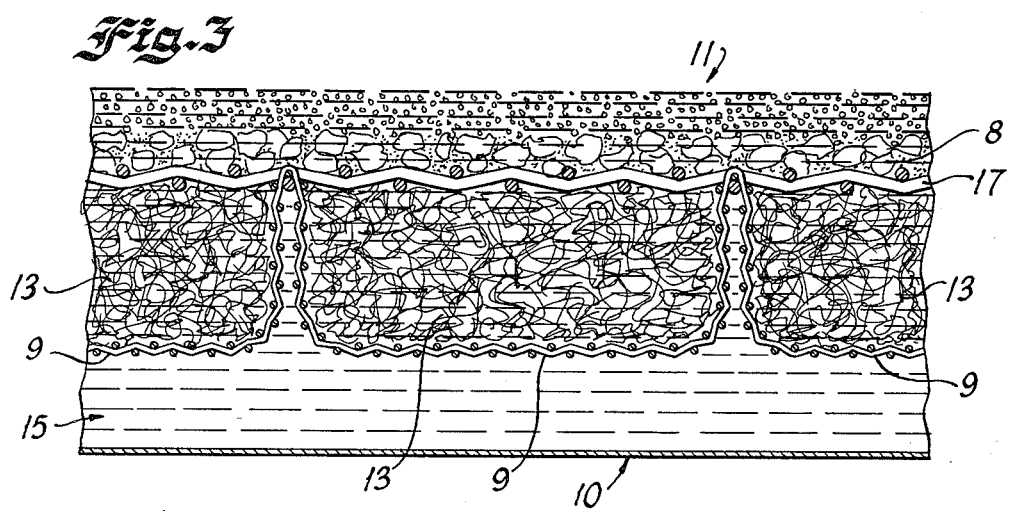
FIG. 3 is a partial sectional view illustrating the details of an alternate form of material mass which may be used in the cell harvesting system.

Although the material mass 13 as depicted in FIG. 1 has been described as consisting of loose fibrous material, such as a mass of cotton fibers, it is pointed out that this material mass may be made up entirely of particulate matter such as sand, crushed rock or very small pebbles, or may be a composite mass of the form illustrated in FIG. 3 of the drawings. As there shown, a mechanical support mesh 9 is provided which at spaced intervals therealong is looped around elemental parts of the screen 17 to form a segmented basket beneath the screen 17. The material mass 13 is disposed within the basket compartments, each of which contains a bottom layer of fibrous material, such as cotton, which is surmounted by a loose particulate layer 8 of sand, crushed stone or small pebbles disposed at least partially on top of the screen 17. With this system arrangement, the high algal cell concentration zone is that portion of the liquid culture medium or slurry which is located within or above the top surface of the layer 8 of particulate material.

Figure 5:
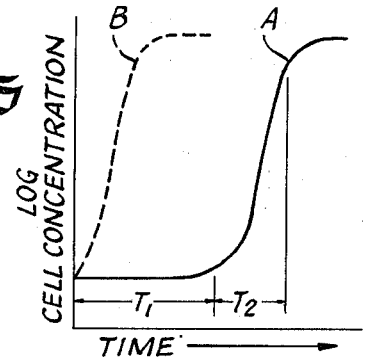
FIG. 5 is a graph typically illustrating the time-cell concentration relationships achieved under the different conditions described below.

The significance of interposing the material mass 13 in the liquid cell growth medium, in terms of enhancement of the described algal cell division process, is well illustrated by the curves shown in FIG. 5 of the drawings, where the algal cell concentration in the liquid cell growth medium 15 contained within the reservoir 10 is plotted as a function of time. In this illustrative example, the degree of cell concentration in the growth medium within the reservoir 10 and without the presence of the material mass 13 in this medium, is represented by the solid line curve A. As this curve shows, for a considerable time after the liquid medium is initially stocked with the algal cells, the degree of cell concentration within the medium increases only very slowly. After a time interval $T_1$ there occurs, during the interval $T_2$, an exponential rise in the degree of cell concentration. Beyond this time interval $T_2$ the degree of cell concentration in the growth medium flattens out indicating that the cell carrying capacity of the medium is substantially saturated.

When a material mass 13 is introduced in the cell growth medium in the manner explained above, the cell concentration-time relationship is typically as shown by the dashed line curve B in FIG. 5 of the drawings. As shown by this curve, the time lag which occurs between the initial cell stocking of the cell growth medium and the start of the exponential rise in cell concentration within the growth medium is materially shortened. This shortened time lag is believed to be caused by collision of the algal cells within the medium with the elemental components of the material mass 13 to accelerate the cell division process in the manner explained above. In a start up operation involving a larger reservoir 10, the lag time $T_1$ between cell stocking of the growth medium and the start of the exponential rise in cell concentration within the growth medium may be very substantial, i.e.

of the order of a week or more, absent the presence of the material mass 13 in the growth medium. Hence by providing this mass in the growth medium, the operational start-up time is significantly reduced.

It has been found that the cell harvest zone 11 need not be submerged in the liquid cell growth medium but may advantageously be disposed adjacent to, but displaced above, the top surface of the liquid medium. Thus and as diagrammatically shown in FIG. 4 of the drawings, the material mass 13 comprises bundles of elongated loose fibers, such as cotton fibers, the lower end segments of which are submerged in the liquid cell growth medium. These fibers extend upward to the harvest zone 11, which is physically displaced above the surface 15 of the cell growth medium. As will be understood from the preceding explanation, liquid movement of the cell containing liquid growth medium from the reservoir 10 to the vertically displaced harvest zone 11 is effected by the capillary interaction between the liquid medium and the fibers forming the material mass 13.

Figure 4:
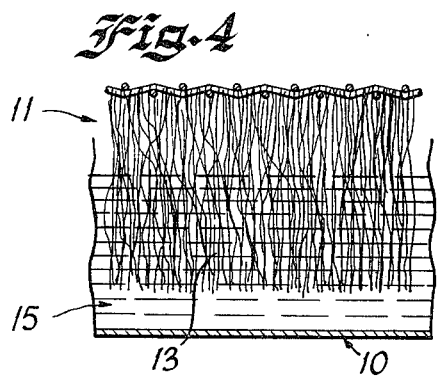
FIG. 4 illustrates still another material mass medium and material mass disposition which may be employed in the cell harvesting system.

One advantage realized by displacing the harvest zone 11 above the surface of the liquid growth medium 15 in the manner illustrated in FIG. 4 and described above is that of very smoothly, and, if desired, very rapidly increasing the salinity of the liquid present in the harvest zone. This increased salinity is achieved through rapid evaporation of the liquid present in the harvest zone as a consequence of air movement, naturally occurring or artificially induced, over the surface of the harvest zone. Also the exposure of the concentrated harvest zone to sunlight or artificial light results in a more rapid rise in the temperature of the liquid in this zone, thereby further to enhance the rate of liquid evaporation from the harvest zone. An increased liquid evaporation rate from the harvest zone 11 may also be achieved by artificially heating this zone through the use of an electrically energized radiant heat source, for example, or through the use of any other suitable heat sources, or air moving devices, or both.

The significance of increasing the salinity of the liquid medium in the harvest zone 11 is pointed out in the above cited U.S. Pat. No. 4,115,949—Mordhay Avron et al. In this patent it is clearly stated that the glycerol content of Dunaliella algal cells increases rather dramatically with an increase in the salinity of the liquid growth medium. Thus by utilizing the material mass arrangement illustrated in FIG. 4 of the drawings and described above to achieve a high degree of salinity of the liquid in the harvest zone 11, a resulting increase in the glycerol content of the harvested algal cells is realized.

The arrangement of the harvest zone 11 above the main body of the liquid whose top surface is 15, as illustrated in FIG. 4, also minimizes the volume of aqueous solution associated with the algal cells situated in the harvest zone 11, whether or not the salinity enhancing evaporation procedure is utilized. As will be understood by anyone skilled in the art of surface and interface science, the length of the harvest zone 11 depends on the size of the individual fibrous strands making up the material mass 13 illustrated in FIG. 4, on the compaction of the material mass 13, on the distribution of interstitial spaces within that material and on the contact angle between the solution 15 and the material substance from which the material mass 13 is constituted.

For the purpose of transferring the concentrated algal cell slurry from the harvest zone 11 to a collection tank or reservoir the system of FIG. 1 may be modified to embody the power energized cell removal means illustrated in FIGS. 6 and 7 of the drawings. As there shown, the side members 12a and 12b are interconnected at their ends by end members, one of which is indicated at 12e, which are adapted to support a liquid displacing partition or scraping member 18 for back and forth movement across the upper surface of the screen 17 between the side member channels 12c and 12d. In the embodiment illustrated, the scraping member is made of relatively heavy inert material, such as rubber covered metal, and is supported at its respective ends by roller assemblies, one of which is generally indicated at 19, the rollers of which are adapted to roll back and forth in roller grooves 20 formed in the top edges of the end members 12e. More specifically, the rollers 19a and 19b of each roller assembly 19 support a carrier 21 to which one end of the scraping member 18 is fixedly connected. Each carrier 21 is provided with an upstanding lug 21a to which an endless actuating cord or belt 22 is fixedly connected. The belt 22 passes around rotatable idler rollers 23 and 24 located adjacent or slightly beyond the ends of the side members 12a and 12b to provide belt segments 22a and 22b which overlie and extend parallel to the upper edges of the end members, such as the end member 12e. The belt 22 is also wrapped once around a drive roller 25 which is rotated by suitable drive means, not shown, in reverse directions between predetermined rotational limits.

With the above described arrangement, rotation of the drive roller 25 in one direction causes movement of the belt 22 in a corresponding direction slowly to move the scraping member 18 from the edge of the collection channel 12c over the top surface of the screen 17 toward the collection channel 12d. When the scraping member 18 reaches the edge of the collection channel 12d, the control means for the drive mechanism which actuates the drive roller 25 functions to effect reverse rotation of the drive roller and thus initiate movement of the scraping member 18 across the surface of the screen 17 back toward the collection channel 12c. It will thus be understood that during normal operation of the system, the scraping member is continuously or intermittently moved slowly back and forth across the screen 17 between the collection channels 12c and 12d.

As the heavy scraping member 18 moves slowly back and forth across the surface of the screen 17, the liquid containing the accumulation of concentrated algal cells which has formed in the harvest zone 11 above the top surface of the screen is pushed by the scraping member into one of the two collection channels 12c or 12d in the manner best illustrated in FIG. 7 of the drawings. Thus as the scraping member 18 moves to the right, as viewed in FIG. 6 of the drawings, toward the side member 12b, the accumulated liquid slurry containing the concentrated algal cells and formed on the top of the screen 17 builds up ahead of the scraping member 17 and is pushed or dumped into the collection channel 12d. Conversely, as the scraping member is moved in the reverse direction, the concentrated algal cell infested liquid slurry is pushed or dumped into the collection channel 12c. Movement of the scraping member 18 across the top surface of the screen 17 also induces circulation of the liquid cell growth medium beneath the screen and through the material mass 13 in the manner indicated by the arrows 26 in FIG. 7 of the drawings. In this context it will be understood that the direction of circulation of the liquid cell growth medium within the confines of the side members 12a and 12b and the end members 12e is reversed as the direction of movement of the scraping member 18 is reversed. Thus a liquid medium sloshing effect is produced within the confines of the side and end members and through the material mass 13, which enhances the algal cell supply in the manner explained above.

Various arrangements may be employed for transferring the concentrated algal cell slurry from the collection channels 12c and 12d to a collection tank or reservoir. In the system arrangement illustrated in FIG. 7 of the drawings, gravity feed is utilized to effect the transfer of the slurry from the collection channels 12c and 12d to a cell collection reservoir or tank 27. More specifically, the ends of the channels 12c and 12d are connected to the tank 27 by means of tubular conduits 28a and 28b which merge into a common conduit 29 the outer end of which opens into the top of the tank 27. Intermediate the ends of the conduit 29, an on-off valve 30 is provided which may be opened to admit liquid slurry into the tank 27 and may be closed to provide for liquid slurry build-up in the channels 12c and 12d and to permit substitution of an empty tank 27 for a slurry filled tank. As will be understood, the collection tank 27 is disposed at a substantially lower level than the conduit terminating ends of the collection channels 12c and 12d in order to insure gravity feed of the slurry from these channels into the tank 27. To further enhance gravity flow of the slurry toward the conduit terminating ends of the collection channels 12c and 12d, these channels are preferably tilted upward with respect to a horizontal plane from the conduit connected ends thereof toward the other ends thereof.

Valves 28c and 28d are respectively located in the conduits 28a and 28b in order to insure that only concentrated slurry is conducted into the common conduit 29. Thus when the displacing member 18 is moved to the right, as seen in FIG. 7, valve 28d is open and valve 28c is closed, whereas when the member 18 is moved to the left, the valve 28c is open and the valve 28d is closed.

Laboratory tests have established beyond reasonable doubt that when the concentrated algal cell liquid medium disposed in a container is subjected to total darkness, the algal cells sediment out of the main body of the liquid and collect in much greater concentrations at the bottom of the container. In order to take advantage of this phenomenon, the collection system illustrated in FIG. 7 and described above may be modified in the manner shown in FIG. 8 of the drawings. As there illustrated, the collection tank 27 is completely light tight, i.e. opaque, so that the cell infested slurry content thereof is subjected to total darkness. As a result, the algal cells are concentrated by sedimentation at the bottom of the tank and in the bottom discharge tubular end 27a of the tank. From this tubular end 27a of the tank, the slurry is delivered through a conduit 31 to the intake side of a motor driven pump 32. The discharge side of the pump 32 is connected through a conduit 33 to the input side of a two-output port valve 34 which can be selectively actuated to deliver all or a portion of the pumped slurry back to the reservoir 10 through a conduit 35 or to a secondary collection tank 36 through a conduit 37. The use of, and actual location of the pump 32 in the system depends on environmental and optimizing factors.

In utilizing the modified collection system illustrated in FIG. 8, the tank 27 is first filled or partially filled with the concentrated algal cell slurry delivered thereto from the collection zone 11 in the manner explained above. As the tank filling operation proceeds, the algal cells sediment out of the liquid medium and collect at the bottom of the tank as well as in the tubular discharge end 27a of the tank and the conduit 31, thereby to increase the cell concentration in these portions of the overall liquid column. In utilizing the illustrated system in batch recycle mode, the two-port valve 34 is first set to discharge the slurry through the conduit 37 to the secondary collection tank 36 following which the pump 32 is activated to effect a transfer of the very highly cell concentrated slurry from the bottom of the tank 27 to the secondary collection tank 36. After a measured time interval sufficient to insure complete transfer of the algal cell concentrate from the bottom of the tank 27 to the secondary collection tank 36, the valve 34 is actuated to shut off liquid flow to the tank 37 and to direct continued liquid delivery by the pump 34 to the conduit 35 and through this conduit back to the reservoir 10. After the tank 27 is partially or completely emptied, the pump is deactivated thus stopping the flow of the slurry from the tank 27 to the valve 34. Thus by carefully manipulating the valve 34 and concurrently activating the pump 32 at measured time intervals determined primarily by the filling time of the tank 27, the very highly concentrated algal cell slurry is delivered to the secondary collection tank 36 and the more dilute cell concentrated slurry, or a portion thereof, is delivered back to the reservoir 10. The purpose of the recycling a portion of the slurry from the collection tank 27 back to the reservoir 10 is explained more fully in specific reference to the system illustrated in FIG. 9 of the drawings.

In utilizing the system illustrated in FIG. 8 in continuous recycle mode, the two-output port valve 34 is set so as to deliver simultaneously one selected volume fraction f of the concentrated slurry to the conduit 37 and thence to tank 36, and another selected volume fraction 1-f to the conduit 35 and thence to the reservoir 10. This continuous recycle mode of operation insures that those cells which are recycled to the growth reservoir 10 are of a strain which is especially suited to their collection in the harvest zone 11, and which also readily sediments in the dark enclosure of tank 27.

In the system arrangement diagrammatically illustrated in FIG. 9 of the drawings, a plurality of reservoirs 10a, 10b, 10c, etc., and a cell collection tank 27a are interconnected by means of conduits 38, 39, 40, etc., and 41 to 47, inclusive, certain of which are provided with on-off valves 48, 49 and 50 to provide for progressive growth multiplication and harvest of the algal cells in the serially related reservoirs and selective recycling of the algal cells from any one of the cell growth reservoirs back into the start-up reservoir 10. As shown, the cell growth reservoirs 10b, 10c, etc., are equipped with harvest zones 11b, 11c, etc., which have material masses 13b, 13c, etc., respectively associated therewith. Structurally, these material mass and harvest zone assemblies may be of the form illustrated in FIGS. 1, 2, 3, 6 and 7 of the drawings and described above.

In utilizing the system shown in FIG. 9, the reservoir 10a containing liquid of the desired salinity, is stocked with the unicellular algal cells, preferably cells of the Dunaliella genus which are allowed to multiply until a saturated cell concentration is approached in the manner explained above in reference to FIG. 5 of the drawings. The valve 38a is then opened to permit the transfer of a portion of the cell concentrate into the reservoir 10b where the cell growth and harvest process is repeated. From the reservoir 10b the cell slurry harvested in the harvest zone 11b may be transferred through the conduit 39 and the valve 39a to the next reservoir in the tandem related reservoir chain through the conduit 40. This reservoir-to-reservoir cell transfer operation is repeated until the last reservoir in the chain is reached. From the harvest zone in this last reservoir the harvested cells may be transferred through the conduit 41 and the valve 41a to the collection tank 27a.

In the modified system arrangement of FIG. 10, a conduit 138, containing a valve 138a is provided which can be used to dilute the concentrate within the reservoir 10b with the fluid contained in the reservoir 10a. Furthermore, the conduit 139, with associated valve 139a, may also be utilized to add fluid from an external source tank (not shown), for example a source tank stocked with a highly concentrated saline solution. Other reservoirs of the cascaded reservoirs may be similarly equipped.

The above described system arrangement of FIGS. 9 and 10 is particularly useful in the growth and harvesting of algal cells. For cells of the Dunaliella genus, by progressively increasing the salinity of the growth medium in the successive reservoirs 10a, 10b, 10c, etc., the glycerol content of the Dunaliella cells is progressively increased. Moreover, the synthesis of useful and desired cellular products other than glycerol by Dunaliella, or by other algae resident in systems of the type described, may be stimulated by the adduction of suitable chemical solutions through the conduits 139a, b, c, etc., without contamination of the reservoir 10a.

Another aspect of the system illustrated in FIG. 9 resides in the ability which it lends to match optimally the cell densities in the harvest zones 11a, b, c, etc., to the cell densities in the reservoirs 10a, b, c, etc., so as to achieve an optimum cell output rate from the system, at the final outlet tank 27a. In this respect the system illustrated in FIG. 9 is analogous to multistage distillation apparatus, the design of which is generally understood by those skilled in the art of separation science.

Another important feature of the system illustrated in FIG. 9 of the drawings resides in the ability selectively to recycle a portion or all of the algal cells harvested in any one of the harvest zones 11b, 11c, etc., back into the start-up reservoir 10a. Thus by selective manipulation of the valves 39a, 40a, etc., 41a, 48, 49 and 50, the cells harvested in any one of the harvest zones 11b, 11c, etc., may be recycled in part or totally back to the start-up reservoir 10a through obvious portions of the conduit network comprising the conduits 46, 44, etc., 42, 43, 45 and 47.

The importance of recycling the algal cells from one or more of the harvest zones back to the cell growth start-up point of the system in the manner explained above in reference to FIGS. 8 and 9 of the drawings will be understood when it is pointed out that the motility, fast swimming, fast dividing and fast climbing are self-selecting characteristics of the cell strains that migrate through one or more of the material masses 13, 13b and 13c into one or more of the associated harvest zones 11, 11b and 11c. Thus the overall performance of the cell growth and harvesting operation is substantially improved by recycling at least a portion of the harvested cells in the manner explained above.

In the foregoing explanation, reference has repeatedly been made to the algal cells of the Dunaliella genus. As will be understood by those skilled in the art, the Dunaliella genus embraces a number of cell species, including tertiolecta, parva, salina and so-called "wild strains", as well as *Dunaliella piercei, Dunaliella primolecta* and *Dunaliella bioculata.* Moreover, certain of the above described systems may be used for the growth and harvesting other forms of motile algal cells, such as Chlamydomonas, which have the characteristic of multiplying by cell division and which exhibit concentrative behavior in materials 13, as described for the case of Dunaliella.

Another method of facilitating the harvesting of algal cells of the indicated character is that of using microorganisms to form fibrous networks in which the algal cells are dispersed at the top of the harvest zone. A harvesting system of this character is diagrammatically illustrated in FIG. 11 of the drawings where the material mass 13 is shown as having a top surface disposed above the surface of the liquid growth medium 15. On the top surface of this material mass, a fibrous network or layer 7 of microorganisms gradually forms as a result of the environmental effect on the microorganisms which migrate through the mass 13 to the top surface of this mass. It has been shown in laboratory tests that after a time interval sufficient to effect the production of a biomass layer 7 of appreciable thickness and consisting of a fibrous network of fungal cells, fungal mycelium, bacteria, algae, and extracellular products, this layer may easily be peeled from the top surface of the material mass 13, rolled up and packaged for removal to a product processing facility. The layer peeling operation may be performed manually or through the use of suitable mechanical means.

It will be understood that in the system of FIG. 11, the microorganisms implanted in the liquid growth medium must be compatible with and nontoxic to the algal cells which are being grown in the medium. For example, if algal cells of the Dunaliella genus are being grown in the liquid growth medium 15, it is believed that such microorganisms as Penicillium sp., Aspergillum sp., Aphanocapsum sp., Cladosporium sp., Pseudomonas sp., Achromobacter sp., Flavobacterium sp., Halobacterium sp., Ectothiorhodospira sp. may be used in the same medium. The system of harvesting shown in FIG. 10 and described above is especially useful for the production of biomass products as well as the described extracellular products.

While the important aspects of the present invention have been described, it will be understood that various modifications may be made in the disclosed systems, processes and apparatus without departing from the true spirit and scope of the invention as defined in the appended claims.

What is claimed and desired to be secured by Letters Patent of the United States is:

1. A system for producing accelerated migration of unicellular motile algal cells from a liquid containing reservoir in which said cells are disposed for multiplication by cell division, comprising a cell harvest zone located adjacent the top surface of the liquid in said reservoir, and a mass of discrete elements connecting said harvest zone with the liquid in said reservoir to provide a migration path which enables cells in said liquid to migrate by self-locomotion from the liquid in said reservoir through said mass to said harvest zone.

2. A system for enhancing the concentration of unicellular algal cells containing glycerol in a predetermined cell harvest zone, comprising a liquid containing reservoir in which said cells are disposed for multiplication by cell division, and substantially static means connecting the liquid source of said cells with said harvest zone to provide a migration path through which cells in said liquid migrate by self-locomotion from said liquid in said reservoir through said static means to said harvest zone.

3. A system as claimed in claim 1 or claim 2, wherein said harvest zone is disposed above and out of contact with the of the top surface of the liquid in said reservoir.

4. A system as claimed in claim 1 or claim 2, wherein said cell harvest zone is of substantially smaller liquid volume than said source or the liquid in said reservoir and is exposed to environmental conditions, whereby the exposure to the air, wind, and illumination of the environment effects relatively rapid evaporation of the liquid present in the harvest zone compared to the rate of evaporation of the source liquid or the liquid in said reservoir.

5. A system as claimed in claim 1, wherein said mass comprises discrete elongated fibers extending downward from said harvest zone into the liquid in said reservoir.

6. A system as claimed in claim 1 or claim 5, wherein the liquid from said source or reservoir rises by capillary action through said mass, thereby providing an uninterrupted cell migration path from said source or reservoir into said cell harvest zone.

7. A system as claimed in claim 5, wherein said elongated fibers are of organic origin.

8. A system as claimed in claim 5, wherein said elongated fibers are of inorganic origin.

9. A system as claimed in claim 1, wherein said mass at least partially comprises a loose mass of particulate material at least partially disposed in the liquid of said reservoir or source.

10. A system as claimed in claim 1 or claim 2, wherein said unicellular algae cells are of the Dunaliella genus.

11. The process of decreasing the time lag of cell division build-up in the early stages of generating a unicellular algal cell culture disposed in a liquid medium and of directing the cells from said liquid medium to a harvest zone located adjacent the surface of said medium, which comprises introducing a collision mass into the liquid medium with which the cells collide to enhance cell division, said mass also providing a preferred travel path for migration of said cells by self-locomotion from said liquid medium through said mass to said harvest zone.

12. The process as claimed in claim 11, wherein said liquid medium and said mass are moved relative to each other, thereby further to enhance the collection efficiency of said cells within said mass.

13. Apparatus for harvesting algal cells from a liquid containing reservoir in which said cells are disposed for multiplication by cell division, comprising means defining a cell harvest zone, means including a mass of discrete elements connecting said harvest zone with the liquid in said reservoir for inducing cell migration by self-locomotion through said mass from said reservoir to said harvest zone to effect increased cell concentration in said harvest zone, means defining a cell collection zone, and transfer means for transferring the concentrated cells from said harvest zone to said cell collection zone.

14. Apparatus as claimed in claim 13, wherein means are provided for inducing movement of the liquid in said reservoir.

15. Apparatus as claimed in claim 13, wherein said transfer means also functions to produce movement of the liquid in said reservoir.

16. Apparatus as claimed in any one of claims 13 to 15, inclusive, wherein the components of the apparatus are so arranged that the liquid in said harvest zone is exposed to open air environmental conditions.

17. Apparatus as claimed in any one of claims 13 to 15, inclusive, wherein means are provided for recycling a portion of the cells in said harvest zone back to the liquid in said reservoir.

18. Apparatus as claimed in any one of claims 13 to 15, inclusive, wherein the liquid in said reservoir and said harvest zone is in the form of a saline solution and said cells are of the unicellular Dunaliella genus, and wherein means are provided for accelerating liquid evaporation from said harvest zone, thereby to produce increased salinity of the liquid in said harvest zone.

19. The process of harvesting and increasing the product yield of algae cells of the Dunaliella genus which are disposed in a saline liquid containing reservoir for multiplication by cell division, which comprises inducing capillary travel of a portion of said cells from said reservoir to a concentrated harvest zone where the concentration of said cells is greatly increased over the cell concentration in said reservoir, and evaporating liquid from said harvest zone to increase the salinity of the remaining liquid in said harvest zone and thus increase the product content of the cells in said harvest zone.

20. The process as claimed in claim 19 wherein the product yield is glycerol.

21. The process as claimed in claim 19 for claim 20, which includes the additional step of feeding a portion of the cells in said harvest zone back to the liquid in said reservoir.

22. Apparatus for harvesting algal cells from a liquid containing reservoir in which said cells are disposed for multiplication by cell division, comprising means defining a cell harvest zone, means including a mass of discrete elements connecting said harvest zone with the liquid in said reservoir for inducing cell migration by self-locomotion from said reservoir through said mass to said harvest zone to effect increased cell concentration in said harvest zone, means defining a cell collection zone, transfer means for transferring the concentrated cells from said harvest zone to said cell collection zone, and means for returning at least a portion of the cells collected in said collection zone to the liquid in said reservoir.

23. Apparatus for harvesting algal cells from a liquid containing reservoir in which said cells are disposed for multiplication by cell division, comprising means defining a cell harvest zone, means including a mass of discrete elements connecting said harvest zone with the liquid in said reservoir for inducing cell migration by self-locomotion from said reservoir through said mass to said harvest zone to effect increased cell concentration in said harvest zone, means defining a cell collection zone, transfer means for transferring the concentrated cells from said harvest zone to said cell collection zone, a discharge outlet connected to said collection zone, and selectively operable means for selectively discharging cells from said collection zone to said discharge outlet or back to the liquid in said reservoir.

24. Apparatus as claimed in either claim 22 or claim 23, wherein the means defining said cell collection zone is completely opaque thus prohibiting light from entering said collection zone, thereby to enhance settlement of the cells in said collection zone to the bottom of said collection zone.

25. Apparatus for growing and harvesting algal cells, comprising a plurality of tandem related liquid containing reservoirs in which said cells are disposed for multiplication by cell division, each of said reservoirs including a cell harvest zone and means including a mass of discrete elements connecting the harvest zone with the liquid in the reservoir for inducing cell migration of self-locomotion from the reservoir through said mass to the harvest zone to effect increased cell through said mass to the harvest zone to effect increased cell concentration in the harvest zone, said transfer means for successively transferring the concentrated cells from the harvest zone of one of said reservoirs to the liquid contained in a following tandem related reservoir.

26. Apparatus for growing and harvesting algal cells, comprising a plurality of tandem related liquid containing reservoirs in which said cells are disposed for multiplication by cell division, each of said reservoirs including a cell harvest zone and means including a mass of discrete elements connecting the harvest zone with the liquid in the reservoir for inducing cell migration by self-locomotion from the reservoir through said mass to the harvest zone to effect increased cell concentration in the harvest zone, transfer means for successively transferring the concentrated cells from the harvest zone of one of said reservoirs to the liquid contained in a following tandem related reservoir, and selectively operable means for returning to the liquid in one of said reservoirs at least a portion of the cells harvested in a following one of the tandem related reservoirs.

* * * * *